United States Patent
Hauck (10) Patent No.: US 10,368,760 B2
(45) Date of Patent: Aug. 6, 2019

(54) MULTI-ELECTRODE IMPEDANCE SENSING

(71) Applicant: St. Jude Medical, Atrial Fibrillation Division, Inc., St. Paul, MN (US)

(72) Inventor: John A. Hauck, Shoreview, MN (US)

(73) Assignee: St. Jude Medical, Atrial Fibrillation Divison, Inc., St. Paul, MN (US)

( * ) Notice: Subject to any disclaimer, the term of this patent is extended or adjusted under 35 U.S.C. 154(b) by 1127 days.

(21) Appl. No.: 14/301,923

(22) Filed: Jun. 11, 2014

(65) Prior Publication Data

US 2014/0364715 A1 Dec. 11, 2014

Related U.S. Application Data

(60) Provisional application No. 61/833,739, filed on Jun. 11, 2013.

(51) Int. Cl.
*A61B 5/04* (2006.01)
*A61B 18/14* (2006.01)
(Continued)

(52) U.S. Cl.
CPC .............. *A61B 5/04* (2013.01); *A61B 5/0538* (2013.01); *A61B 5/063* (2013.01); *A61B 5/6843* (2013.01);
(Continued)

(58) Field of Classification Search
CPC ... A61B 5/6843; A61B 5/0538; A61B 5/6887; A61B 18/1206; A61B 18/1492;
(Continued)

(56) References Cited

U.S. PATENT DOCUMENTS 4,587,975 A * 5/1986 Salo ..................... A61B 5/0535
600/506
5,341,807 A 8/1994 Nardella
(Continued)

FOREIGN PATENT DOCUMENTS

CN 101534736 9/2009
CN 102355856 2/2012
(Continued)

OTHER PUBLICATIONS

Assambo, C. et al., "Determination of the Parameters of the Skin-Electrode Impedance Model for ECG Measurement", Proceedings of the 6th WSEAS Int. Conf. on Electronics, Hardware, Wireless and Optical Communications, pp. 90-95, Feb. 2007.

*Primary Examiner* — Lee S Cohen
*Assistant Examiner* — Erin M Cardinal
(74) *Attorney, Agent, or Firm* — Dykema Gossett PLLC (57) ABSTRACT

A system and method for assessing contact between a medical device and tissue may comprise an electronic control unit (ECU) configured to be coupled to a medical device, the medical device comprising a first electrode and a second electrode. The ECU may be further configured to select the first electrode as an electrical source and the second electrode as an electrical sink, to cause an electrical signal to be driven between the source and sink, to detect respective electric potentials on the first electrode and the second electrode while the electrical signal is driven, and to determine an impedance respective of one of the first electrode and the second electrode according to both of the respective electric potentials.

16 Claims, 4 Drawing Sheets

(51) Int. Cl.
    *A61B 5/06*     (2006.01)
    *A61B 5/00*     (2006.01)
    *A61B 5/053*    (2006.01)
    *A61B 90/00*    (2016.01)
    *A61B 18/00*    (2006.01)

(52) U.S. Cl.
    CPC .......... *A61B 5/6857* (2013.01); *A61B 5/6885* (2013.01); *A61B 18/1492* (2013.01); *A61B 90/06* (2016.02); *A61B 2018/00577* (2013.01); *A61B 2018/00875* (2013.01); *A61B 2090/065* (2016.02)

(58) Field of Classification Search
    CPC .......... A61B 2018/00875; A61B 2018/00577; A61B 5/6885; A61B 5/06; A61B 5/061; A61B 5/063; A61B 5/065; A61B 5/068; A61B 5/7221; A61B 2090/065
    See application file for complete search history.

(56) References Cited

U.S. PATENT DOCUMENTS

| | | | |
|---|---|---|---|
| 5,469,857 A * | 11/1995 | Laurent | A61B 5/0422 600/509 |
| 6,129,669 A * | 10/2000 | Panescu | A61B 5/06 600/424 |
| 6,391,024 B1 | 5/2002 | Sun et al. | |
| 6,546,270 B1 | 4/2003 | Goldin et al. | |
| 7,263,397 B2 | 8/2007 | Hauck et al. | |
| 8,403,925 B2 | 3/2013 | Miller et al. | |
| 2004/0230131 A1* | 11/2004 | Kassab | A61B 5/053 600/547 |
| 2007/0060833 A1 | 3/2007 | Hauck | |
| 2007/0123764 A1* | 5/2007 | Thao | A61B 18/14 600/374 |
| 2008/0275442 A1* | 11/2008 | Paul | A61B 18/1492 606/41 |
| 2008/0312713 A1 | 12/2008 | Wilfley et al. | |
| 2009/0158852 A1* | 6/2009 | Paul | A61B 5/042 73/723 |
| 2010/0010612 A1* | 1/2010 | Gelbart | A61F 2/958 623/1.11 |
| 2010/0168560 A1* | 7/2010 | Hauck | A61B 5/06 600/424 |
| 2010/0217132 A1* | 8/2010 | Ellingwood | A61B 5/053 600/481 |
| 2011/0306867 A1* | 12/2011 | Gopinathan | A61B 5/02007 600/407 |
| 2012/0078342 A1* | 3/2012 | Vollkron | A61B 5/0538 623/1.11 |
| 2012/0172702 A1 | 7/2012 | Koyrakh et al. | |
| 2012/0203169 A1 | 8/2012 | Tegg | |

FOREIGN PATENT DOCUMENTS

| | | |
|---|---|---|
| EP | 1169976 | 1/2002 |
| WO | 2000/078239 | 12/2000 |
| WO | 2010/020958 | 2/2010 |

* cited by examiner

MULTI-ELECTRODE IMPEDANCE SENSING

CROSS-REFERENCE TO RELATED APPLICATION

This application claims the benefit of U.S. provisional application No. 61/833,739, filed 11 Jun. 2013, which is hereby incorporated by reference in its entirety.

BACKGROUND a. Technical Field

The instant disclosure relates to electrical impedance-based contact sensing, including contact between tissue and electrodes disposed in or on a medical device.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site such as, for example, a site within the patient's heart. The catheter typically carries one or more electrodes, which may be used for ablation, diagnosis, and the like.

In many procedures, it may be beneficial to know the contact status of an electrode (e.g., in contact with tissue, in a blood pool) on a catheter. For example, in an electrophysiology mapping procedure, the electrical signal present on an electrode may vary depending on whether the electrode is in contact with tissue, or adjacent to the tissue in a blood pool, and that difference may be accounted for in software. In another example, in an ablation procedure, it may be desirable to only drive an ablation current when an electrode is in contact with the tissue to be ablated.

One existing methodology that may be used to determine whether an electrode on a catheter is in contact with tissue includes driving a current between the electrode and an electrode elsewhere within the patient (e.g., at a stable position within the patient) or on the exterior of the patient (e.g., on the patient's skin) and assessing the impedance between the electrodes. To determine an impedance between those electrodes, the electric potential of the electrode on the medical device may be referenced to a third electrode, which may also be elsewhere within the patient or on the exterior of the patient.

The foregoing discussion is intended only to illustrate the present field and should not be taken as a disavowal of claim scope.

BRIEF SUMMARY

An embodiment of a system for assessing contact between a medical device and tissue may comprise an electronic control unit (ECU) configured to be coupled to a medical device, the medical device comprising a first electrode and a second electrode. The ECU may be further configured to select the first electrode as an electrical source and the second electrode as an electrical sink, to cause an electrical signal to be driven between the source and sink, to detect respective electric potentials on the first electrode and the second electrode while the electrical signal is driven, and to determine an impedance respective of one of the first electrode and the second electrode according to both of the respective electric potentials.

An embodiment of a method for determining impedances respective of a first electrode and a second electrode, the first and second electrodes disposed on an elongate medical device, may comprise a number of steps. A first step may include driving an electrical signal between the first electrode and the second electrode and a second step may include measuring respective electric potentials on the first electrode and the second electrode while driving the electrical signal. A third step may include determining impedances respective of the first electrode and the second electrode, both impedances determined according to both of the respective electric potentials.

An embodiment of a system may comprise an elongate medical device comprising a shaft and a first electrode and a second electrode disposed on or in the shaft. The system may further comprise an ECU coupled to the elongate medical device and configured to select the first electrode as an electrical source and the second electrode as an electrical sink, to cause an electrical signal to be driven between the source and sink, to detect respective electric potentials on the first electrode and the second electrode while the electrical signal is driven, and to determine an impedance respective of one of the first electrode and the second electrode according to the respective electric potentials.

Systems and methods according to the present disclosure may improve on known systems and methods for assessing contact between a medical device and tissue by reducing the electrical current to which the patient is exposed. Further, systems and methods according to the present disclosure may provide improved reliability relative to known systems and methods by reducing the path length of one or more driven currents.

DETAILED DESCRIPTION

Figure 1:
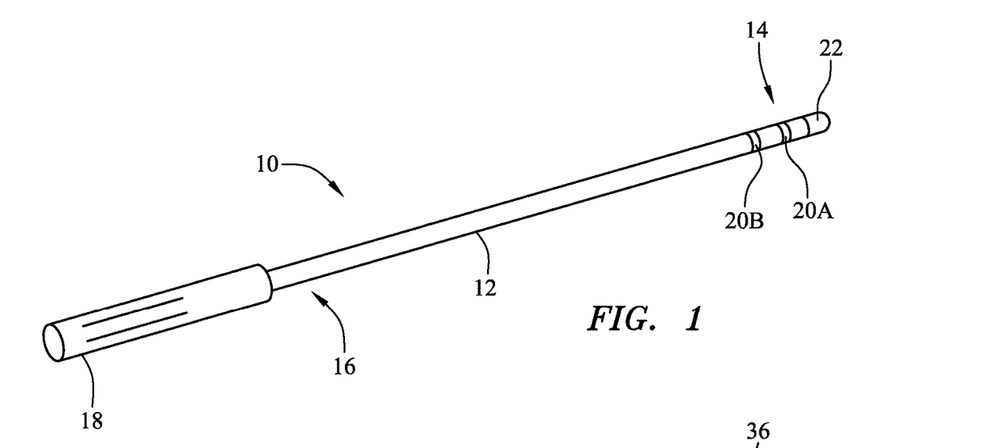
FIG. 1 is an isometric view of an exemplary embodiment of an elongate medical device having multiple electrodes.

Referring now to the figures, in which like numerals indicate the same or similar elements in the various views, FIG. 1 is an isometric view of an exemplary embodiment of the elongate medical device 10. The elongate medical device 10 may comprise, for example, a diagnostic and/or therapy delivery catheter, an introducer or sheath, or other like devices. For purposes of illustration and clarity, the description below will be with respect to an embodiment wherein the elongate medical device 10 comprises a catheter (i.e., catheter 10). It will be appreciated, however, that embodiments wherein the elongate medical device 10 comprises an elongate medical device other than a catheter remain within the spirit and scope of the present disclosure.

The catheter 10 may comprise a shaft 12 having a distal end portion 14 and a proximal end portion 16. The catheter 10 may be configured to be guided through and disposed in the body of a patient. Accordingly, the proximal end portion 16 may be coupled to a handle 18, which may include features to enable a physician to guide the distal end portion 14 to perform a diagnostic or therapeutic procedure such as, for example only, an ablation or mapping procedure on the heart of the patient. Accordingly, the handle 18 may include one or more manual manipulation mechanisms such as, for example, rotational mechanisms and/or longitudinal mechanisms, coupled to pull wires for deflecting the distal end portion 14 of the shaft 12. Exemplary embodiments of manipulation mechanisms, pull wires, and related hardware are described, for example only, in U.S. patent application publication no. 2012/0203169, hereby incorporated by reference in its entirety. The handle 18 may further include one or more electromechanical connectors for coupling to a mapping and navigation system, an ablation generator, and/or other external systems. The handle 18 may also include one or more fluid connectors for coupling to a source and/or destination of fluids such as, for example only, a gravity feed or fixed or variable-rate pump.

The distal end portion 14 of the shaft 12 may include a number of ring electrodes 20A, 20B (which may be referred to herein individually and generically as a ring electrode 20 or in the multiple as the ring electrodes 20) and a tip electrode 22 for applying ablation energy to tissue, acquiring electrophysiology data from tissue, determining the position and orientation (P&O) of the shaft 12, and/or other purposes. The electrodes 20, 22 may be coupled to electrical wiring within the shaft 12, which may extend to the handle 18 and to electromechanical connectors for coupling to external systems. The ring electrodes 20 may be placed about six (6) millimeters away from each other (e.g., measuring from the center of one ring electrode 20 to the center of another ring electrode 20 along the longitudinal axis of the shaft 12), and each may have a radius of about one (1) millimeter, in an embodiment.

The distal end portion 16 of the shaft 12 may also include one or more fluid ports or manifolds for distributing or collecting fluids such as, for example only, irrigation fluid during an ablation procedure. The fluid ports may be fluidly coupled with one or more fluid lumens extending through the shaft 12 to the handle 18 and a fluid connector for coupling to external fluid sources and/or destinations. One or more lumens may also be provided through the shaft 12 for passing a second elongate medical device. In some embodiments, for example, the elongate medical device 10 may comprise an introducer that includes at least one lumen configured to receive another device such as a catheter or probe.

Figure 2:
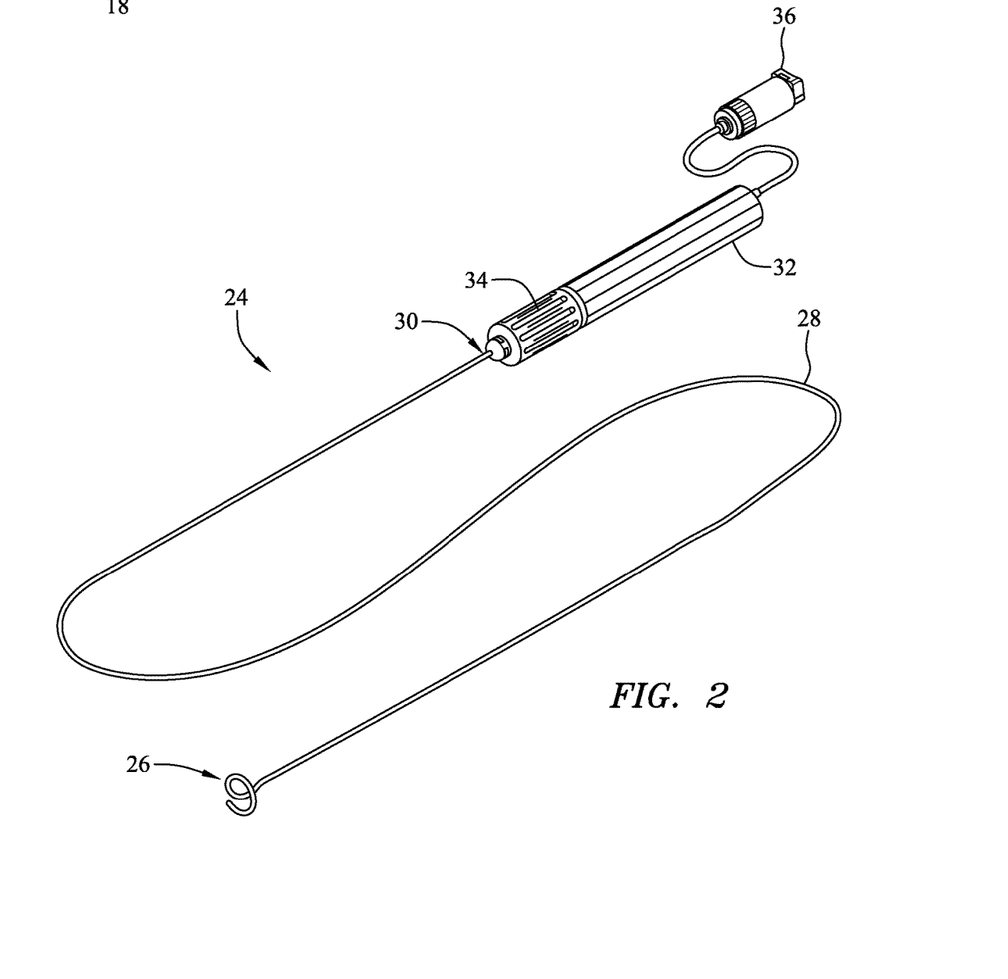
FIG. 2 is an isometric view of an exemplary embodiment of an elongate medical device having a distal lariat portion.
Figure 3:
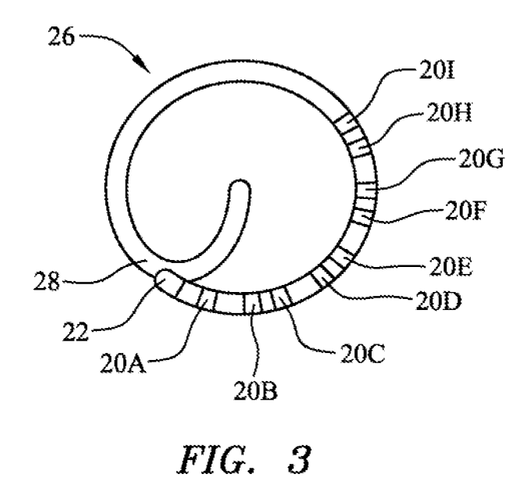
FIG. 3 is an end view of the distal end portion of the elongate medical device of FIG. 2, illustrating multiple electrodes that may be used on the device.

FIG. 2 is an isometric view of another exemplary embodiment of an elongate medical device 24, the elongate medical device 24 having a distal lariat portion. FIG. 3 is a distal end view of a distal end portion 26 of the shaft 28 of the device 24. For purposes of illustration and clarity, the description below will be with respect to an embodiment wherein the elongate medical device 24 comprises a catheter (i.e., catheter 24). It will be appreciated, however, that embodiments wherein the elongate medical device comprises an elongate medical device other than a catheter remain within the spirit and scope of the present disclosure.

Referring to FIGS. 2 and 3, the catheter 24 may comprise a shaft 28 having a distal end portion 26 and a proximal end portion 30. The catheter 24 may be configured to be guided through and disposed in the body of a patient. Accordingly, the proximal end portion 30 of the shaft 28 may be coupled to a handle 32, which may include features to enable a physician to guide the distal end portion to perform a diagnostic or therapeutic procedure such as, for example only, an ablation or mapping procedure on the heart of the patient. Accordingly, the handle 32 may include one or more manual manipulation mechanisms 34 such as, for example, rotational mechanisms and/or longitudinal mechanisms, coupled to pull wires for deflecting the distal end portion of the shaft. Exemplary embodiments of manipulation mechanisms, pull wires, and related hardware are described, for example only, in U.S. patent application publication no. 2012/0203169, referenced above. The handle 32 may further include one or more electromechanical connectors for coupling to a mapping and navigation system, an ablation generator, and/or other external systems. The handle 32 may also include one or more fluid connectors 36 for coupling to a source and/or destination of fluids such as, for example only, a gravity feed or fixed or variable-rate pump.

The distal end portion 26 of the shaft 28 may have a portion having a lariat shape. In an embodiment, the lariat shape may be formed by, for example, a shape memory wire disposed within the shaft. A tip electrode 22 and a number of ring electrodes 20A, 20B, 20C, 20D, 20E, 20F, 20G, 20H, 20I (which, again, may be referred to herein individually and generically as a ring electrode 20 or in the multiple as the ring electrodes 20) may be disposed on the distal end portion 26 of the shaft 28, in an embodiment. For example, the tip electrode 22 and ring electrodes 20 may be disposed on the lariat portion of the shaft 28. In an embodiment, the distal end portion 26 may include nine (9) ring electrodes 20 (i.e., a "decapolar" catheter having ten total electrodes, as illustrated in FIG. 3) or nineteen (19) ring electrodes 20 (i.e., a "duo-decapolar" catheter having twenty total electrodes). Like the catheter 10 illustrated in FIG. 1, the electrodes 20, 22 on the catheter 24 illustrated in FIGS. 2 and 3 may be used for applying ablation energy to tissue, acquiring electrophysiology data from tissue, determining the position and orientation (P&O) of the shaft, and/or other purposes. The electrodes 20, 22 may be coupled to electrical wiring within the shaft 28, which may extend to the handle 32 and to electromechanical connectors for coupling to external systems. The ring electrodes 20 may be placed in pairs, in an embodiment, with the two electrodes 20 in a pair disposed a first distance away from each other along the length of the shaft 28, and non-pair electrodes 20 separated by a second distance along the length of the shaft 28. For example, electrodes 20B and 20C may be considered a first pair, electrodes 20D and 20E may be considered a second pair, and so on. The first distance may be less than the second distance, in an embodiment. For example, the first distance may be about one (1) mm, and the second distance may be about 4.5 mm.

The catheters 10, 24 illustrated in FIGS. 1-3 are exemplary in nature only. The teachings of the present disclosure may find use with numerous other medical devices, such as circular mapping catheters, other known mapping and diagnostic catheters, and other known medical devices, in embodiments. Furthermore, two or more ring electrodes may be provided on various embodiments of the medical device, and the methods, steps, techniques, and algorithms discussed below may find use with potentially many electrodes on the medical device.

An elongate medical device having multiple electrodes, such as the catheter 10 or the catheter 24, may find use in a system for assessing a state of contact between the elongate medical device and the tissue of a patient. As mentioned in the Background, in some known systems, an electrical current may be driven between an electrode on an elongate medical device disposed within the body and a cutaneous electrode to assess such contact. The electric potential on the in-body electrode may be measured with reference to a third electrode (e.g., another cutaneous electrode), and an impedance may be calculated, which impedance may indicate a contact state. Such a system and methodology may be improved upon by a system for assessing a contact state according to an electrical current driven between two electrodes on the same device (e.g., on the same elongate medical device within the patient's body).

Figure 4:
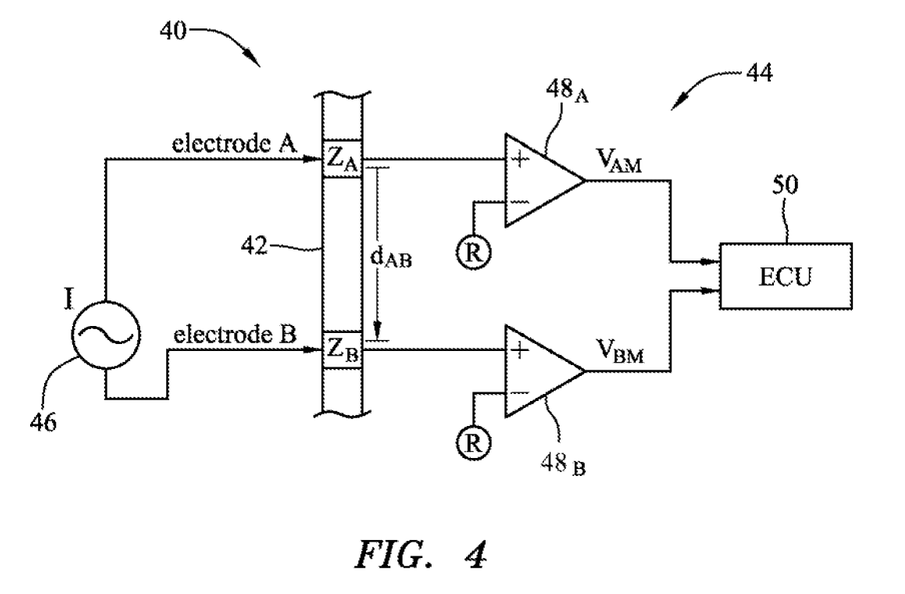
FIG. 4 is a diagrammatic view of an exemplary embodiment of a system for determining a biological impedance at two electrodes on an elongate medical device.

FIG. 4 is a diagrammatic view of a system 40 for assessing a contact state according to an electrical current driven between two electrodes on the same device. The system 40 may include a medical device 42 comprising at least two electrodes A, B having respective impedances $Z_A$, $Z_B$, a detection amplifier 44, and a signal generator 46. The detection amplifier may include, in an embodiment two operational amplifiers (op amps) $48_A$, $48_B$, a reference electrode R, and an impedance sensor in the form of an electronic control unit (ECU) 50. In an embodiment, the signal generator may be incorporated in or may be considered a part of the detection amplifier 44.

The medical device 42 may be or may include an elongate medical device, in an embodiment. For example, the medical device 42 may be the catheter 10 (see FIG. 1) or the catheter 24 (see FIGS. 2 and 3). The medical device 42 may have exactly two electrodes A, B or more than two electrodes. For example, the medical device 42 may have three (3) electrodes, like the catheter 10 illustrated in FIG. 1, may have ten (10) electrodes, like the catheter 24 illustrated in FIGS. 2 and 3, or may have some other number of electrodes.

The electrodes A, B may be any two electrodes on the device, in an embodiment. For example, referring to FIGS. 1 and 4, the electrodes A, B may be the tip electrode 22 and the first ring electrode 22A. Alternatively, referring to FIGS. 3 and 4, the electrodes A, B may be two ring electrodes 20D and 20E, or 20F and 20G, etc.

The signal generator 46 may be configured to generate (e.g., among other signals), an excitation signal across the electrodes A, B (i.e., using one electrode as a source and the other as a sink). In an embodiment, the excitation signal may have a frequency within a range from about 1 kHz to over 500 kHz, more preferably within a range of about 2 kHz to 200 kHz, and even more preferably about 20 kHz. In an embodiment, the excitation signal may be a constant current signal, preferably in the range of between 20-200 µA, and more preferably about 100 µA.

The ECU 50 may include conventional filters (e.g., bandpass filters) to block frequencies that are not of interest, but permit appropriate frequencies, such as the excitation frequency, to pass, as well as conventional signal processing software used to obtain the component parts of the measured complex impedance. Accordingly, the impedance sensor 50 may include a memory storing such signal processing software and a processor configured to execute the signal processing software, in an embodiment.

The ECU 50 may include any processing apparatus such as, as noted above, a memory and a processor. Additionally or alternatively, the impedance sensor may include an application-specific integrated circuit (ASIC), programmable logic device (PLD), field-programmable gate array (FPGA), and/or other processing device.

The detection amplifier 44 may have a positive polarity connector which may be electrically connected to a first electrode A and a negative polarity connector which may be electrically connected to a second electrode B. The positive and negative polarity connectors may be disposed relative to the other components of the detection amplifier 44 so as to form the circuit diagrammatically shown in FIG. 4 when connected with the electrodes A, B. It should be understood that the term connectors as used herein does not imply a particular type of physical interface mechanism, but is rather broadly contemplated to represent one or more electrical nodes.

The detection amplifier may drive a current between electrodes A, B on the same device to assess a contact state between the electrodes A, B and tissue. Impedances may be calculated based on those driven currents to determine a contact state. The system may be configured to execute the method 60 of FIG. 5, as described below, to determine impedances respective of the first and second electrodes A, B to determine a contact state.

Figure 5:
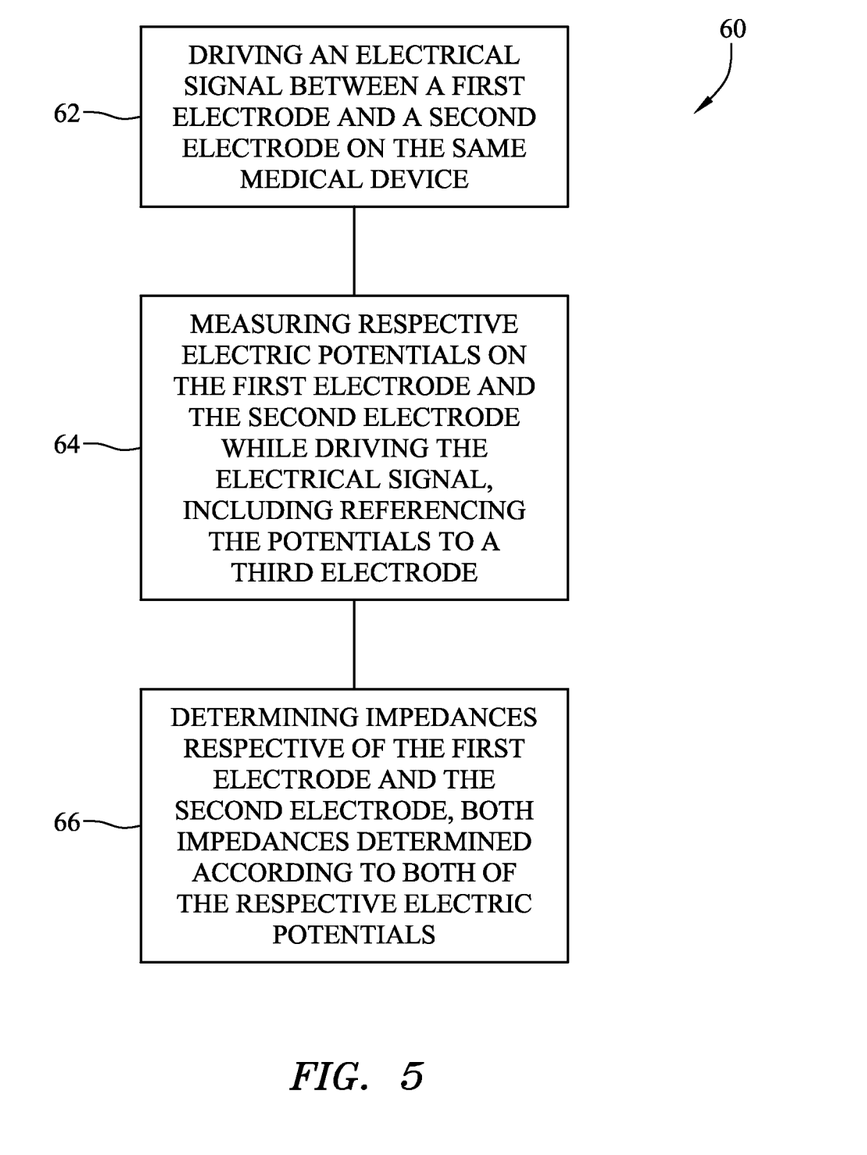
FIG. 5 is a flow chart illustrating an exemplary embodiment of a method of determining a biological impedance at two electrodes on an elongate medical device.

FIG. 5 is a flow chart illustrating a method 60 of determining impedances respective of a pair of electrodes. Referring to FIGS. 4 and 5, the electrodes referred to in the method 60 may be electrodes A and B (shown in FIG. 4). The method 60 will be described with reference to electrodes A and B. It should be understood, though, that the method 60 may find use with numerous different electrode arrangements—both adjacent and non-adjacent electrodes, ring and other types of electrodes, etc. Additionally, in embodiments, more than two electrodes may be used in variations of the method 60.

The method 60 may begin with a step 62 of driving an electrical signal between electrodes A and B, with one of electrodes A and B selected as a source, and the other as a sink. The source and sink selection may be made by the ECU 50, and the current driven by the signal generator 46. The signal may have predetermined characteristics (e.g., frequency and amplitude). In an embodiment, the signal may have a frequency within a range from about 1 kHz to over 500 kHz, more preferably within a range of about 2 kHz to 200 kHz, and even more preferably about 20 kHz. In an embodiment, the signal may be a constant current signal, preferably in the range of between 20-200 µA, and more preferably about 100 µA.

The method 60 may further include a step 64 of measuring respective electric potentials on electrodes A and B while driving the current between electrodes A and B. The potentials may be measured by a detection amplifier, in an embodiment. The detection amplifier may present a very high impedance (for example, about 100 kΩ or more, in an embodiment, and/or 50 times or more greater than the nominal impedance of one of the electrodes A, B, in an embodiment, and/or 100 times or more greater than the nominal impedance of one of the electrodes A, B, in an embodiment) relative to the path between electrodes A and B, so the effect of measurements with the detection amplifier on the potential on the electrodes A, B may be negligible.

The measuring step 64 may further include referencing the measured electric potentials to a reference electrode, such as electrode R (shown in FIG. 4). Reference electrode R may be a cutaneous electrode, such as a body patch electrode, in an embodiment. Alternatively, the reference electrode R may be another in-patient electrode. Such referencing may be performed, in an embodiment, by inputting the potential on electrode A into a first input of the first op amp $48_A$, the potential on electrode B into a first input of the second op amp $48_B$, and the potential on the reference electrode into respective second inputs on both the first op amp $48_A$ and the second op amp $48_B$. The output of the op amps $48_A$, $48_B$ may be input to the ECU 50, in an embodiment, for impedance determinations, contact assessment, and/or other calculations. In another embodiment, hardware separate from the ECU 50 may be provided to perform some or all of the impedance and/or contact determinations and other functions of the detection amplifier described above and/or below.

For driving the current between electrodes A and B and determining electric potentials on electrodes A and B, well known methods of driving a current at a particular carrier frequency and synchronously demodulating the respective potentials on electrodes A and B may be used. The detection amplifier may amplify the signals manifest on each electrode A, B, and after demodulation a voltage related to the impedance of each electrode is available.

In the case of electrode B, the recovered voltage will be negative (i.e., assuming electrode A is selected as the source and B as the sink), so a trivial conversion to a positive quantity may be applied by the ECU 50 or other device. Since the current source-sink electrode pair may comprise a closely spaced dipole, the potential at the reference electrode R with respect to the dipole will be low, and thus the physical location of R may vary with little effect on the voltages between A and R and B and R.

The method 60 may further include a step 66 of determining impedances at each of the electrodes according to the measured electric potentials on the electrodes. The determining step may include mathematically accounting for the effects of each electrode A, B, on the potential measured on the other electrode A, B. Such accounting may include, among other things, considerations of the radius of each electrode A, B and the distance between the electrodes A, B.

The electric potential measured on each electrode A, B will carry a component of influence from the potential at the other electrode A, B. Generally, for purposes of assessing the impedance of a given electrode, influence from the neighboring electrode is not desired, so this component of potential may be accounted for and corrected. As a result, measurements based on a current driven between two electrodes A, B on the same medical device may be more predictable than measurements based on a current driven between an electrode (e.g., electrode A) and a cutaneous electrode, in which undesired effects on the potential measured on the electrode (e.g., electrode A) (due to, for example, unpredictable variations in the impedance of the patient's body) are more difficult to account for and correct. As a result, contact assessments based on a current driven between electrodes A, B may be more accurate than contact assessments based on a current driven between an electrode on a catheter and an exterior electrode.

For a given electrode geometry for which impedance is measured at a sufficiently high frequency, such as twenty (20) kHz or higher for platinum iridium electrodes, for example only, the potential measured for a current driven between electrodes A, B may be essentially resistive in a pure saline or blood medium, and may reflect the electrode's geometry and the solution conductivity. For example, a spherical electrode in a homogeneous medium will have an electric potential for a current driven through the electrode according to equation (2) below:

$$V = \frac{\rho I}{4\pi r} \quad (2)$$

where V is electric potential, I is the applied current, ρ is the media resistivity, and r is the distance from the center of the electrode to the point on the electrode at which the potential measurement is made. The measured impedance may be taken as the measured potential on the electrode divided by the applied current, as set forth in equation (3) below:

$$Z = \frac{V}{I} \quad (3)$$

The spherical electrode model of equation (2) may be utilized even for certain non-spherical electrodes such as, for example, ring electrodes. It has been shown in computer models and testing that, for typical ring electrodes used in heart mapping catheters, of six (6) or seven (7) French diameter (i.e., a radius of about one (1) millimeter (mm)), and ring thicknesses of one (1) or two (2) mm, the spherical electrode model applies with acceptable accuracy. The spherical model may apply to ring electrodes of different diameters and thicknesses, as well. In both spherical and ring electrodes, the electrode driven with a current creates a potential that varies inversely with distance in a predictable manner.

In the spherical model (which, as noted above, may be applied to ring electrodes), a current may be driven between a pair of electrodes A, B, with respective electrode radii $r_A$ and $r_B$ and local resistivity values $\rho_A$ and $\rho_B$. Local resistivity may vary between different locations within a patient, leading to a change in computed impedance respective of the electrode A, B, which may be used to determine the position of the electrode A, B. For example, an electrode in blood will encounter a lower local resistivity than an electrode embedded in tissue, and this difference may be manifest in the impedance measurement.

If a current is driven between electrodes A and B, a voltage measurement made on one of them (with respect to a distant or infinite reference, such as reference electrode R) will, by virtue of superposition, contain both the potential owing to the current emitted from the measured electrode (the value of which is shown in equation (2)), as well as potential due to the current through the second electrode. The distance between electrodes A, B (from the center of electrode A to the center of electrode B), denoted $d_{AB}$ (see FIG. 3), may be relevant to the amount that the current through one electrode (e.g., the sink) affects the potential measured on the other electrode (e.g., the source). Both electrode radii $r_A$ and $r_B$ and the distance between the electrodes $d_{AB}$ may be stored (e.g., in the memory) or otherwise known (e.g., by the ECU 50). It may be assumed that the electrodes' radii are small enough that the electrodes do not overlap (again, modeling the electrodes A, B as spheres), satisfying equation (4) below:

$$r_A + r_B < d_{AB} \quad (4)$$

Electrode A may have a measured potential that is dependent on the current flowing through both electrodes A and B, as well as the physical configuration of electrode A (i.e., radius and local resistivity), the local resistivity electrode B, and the distance between electrodes A and B. The measured potential on electrode A, $V_{Am}$, may be characterized according to equation (5) below:

$$V_{Am} = \frac{\rho_A I}{4\pi r_A} + \frac{\rho_B I}{4\pi d_{AB}} \quad (5)$$

where the first term on the right hand side of equation (5) follows directly from equation (2), and the second term on the right hand side of equation (5) results from the potential on electrode B. As shown in FIG. 3, $V_{Am}$ is the voltage that results from referencing the potential on electrode A to the potential on reference electrode R. Analogously, the measured potential $V_{Bm}$ on electrode B may be characterized according to equation (6) below:

$$V_{Bm} = \frac{\rho_B I}{4\pi r_B} + \frac{\rho_A I}{4\pi d_{AB}} \qquad (6)$$

In both equations (5) and (6), it is desirable to account for and remove the influence of the other electrode (i.e., the influence of electrode B on the potential measured for electrode A, and vice-versa) by solving for the first term in the right hand side of equations (5) and (6). Because all quantities in equations (5) and (6) are known (i.e., stored or measured) except for the resistivity values $\rho_A$ and $\rho_B$, the resistivity values may be solved for. Doing so, and collecting certain terms on the left hand side, results in equation (7) below:

$$\frac{\rho_A I}{4\pi r_A} = \frac{d_{AB} V_{Am} - r_B V_{Bm}}{d_{AB} - \frac{r_A r_B}{d_{AB}}} + \frac{\rho_B I}{4\pi} \qquad (7)$$

In comparing equation (7) to equation (2), it can be seen that the left hand side of equation (7) is the desired potential on electrode A, free of the influence of electrode B. Accordingly, equation (7) may be re-written as equation (8) below for the potential on electrode A:

$$V_A = \frac{d_{AB} V_{Am} - r_B V_{Bm}}{d_{AB} - \frac{r_A r_B}{d_{AB}}} \qquad (8)$$

A counterpart equation for the potential on electrode B, free of the influence of electrode A, may be written as equation (9) below:

$$V_B = \frac{d_{AB} V_{Bm} - r_A V_{Am}}{d_{AB} - \frac{r_A r_B}{d_{AB}}} \qquad (9)$$

Thus, for each potential measured as a current is driven between electrodes A and B, equations (8) and (9) may be solved (e.g., by the ECU 50) to determine the voltages on each of electrodes A and B (relative to reference electrode R). Accordingly, equations (8) and (9) may be stored in the memory of the ECU 50 for execution by the processor of the ECU 50. Those voltages may be applied to equation (2) to determine impedances respective of each of electrode A and B (again, by the ECU 50, for example). Based on those impedances, a contact state between electrodes A and B and the tissue of a patient may be assessed. Such measurements may be carried out numerous times, multiplexed with the patch excitation and measurement process described above. Furthermore, such measurements may be carried out for numerous sets of electrodes A and B.

For electrodes other than ring and spherical electrodes, the calculations according to the equations above may be modified to account for the particular geometry of the electrode.

Alternatively, instead of mathematically accounting for the effect of one electrode on the electric potential on the other electrode, a compensation factor may be determined experimentally.

In an embodiment, the steps of the method 60 may be carried out repeatedly for numerous different pairs of electrodes to determine a contact state for each of those electrodes. For example, referring to FIGS. 3 and 5, the steps of the method 60 may first be carried out on electrodes 22 and 20A, then on 20B and 20C, then on 20D and 20E, and so on. Any two electrodes on the catheter 24 may be used in the method 60, in an embodiment (i.e., the method 60 may be applied to adjacent electrodes, but is not limited to use with adjacent electrodes).

Referring to FIG. 4, the system 40 may be a standalone system, in an embodiment. Alternatively, the system 40, or the functionality of the system 40, may be incorporated into a system having additional functionality. For example, the functionality of the system 40 may be incorporated into a mapping and navigation system.

Figure 6:
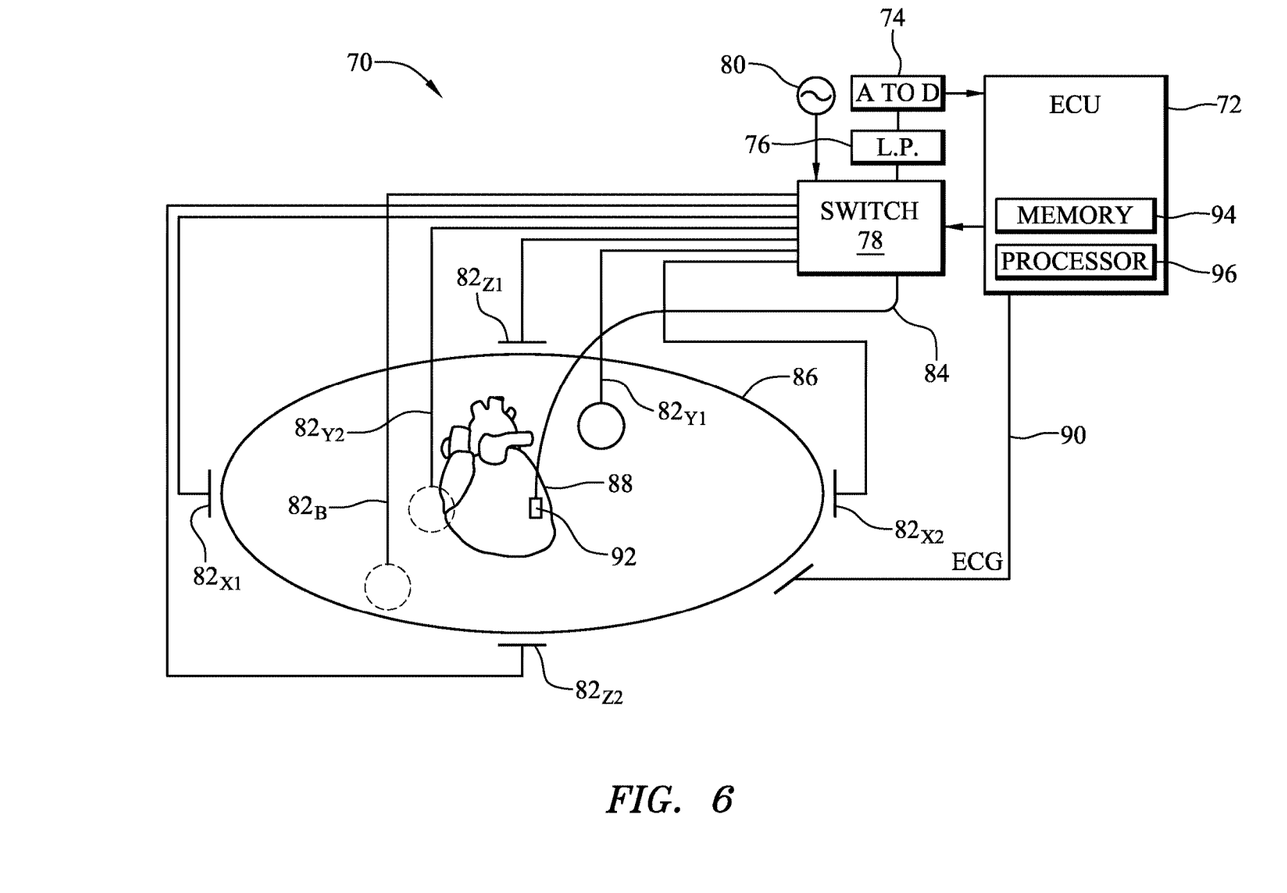
FIG. 6 is a diagrammatic depiction of an exemplary embodiment of a mapping and navigation system that may include functionality for determining a biological impedance at two electrodes on an elongate medical device.

FIG. 6 is a diagrammatic depiction of an embodiment of an exemplary mapping and navigation system 70 that may incorporate the contact sensing functionality of the system 40 (see FIG. 4) and the method 60 (see FIG. 5), in addition to various other functionality including, but not limited to, determining the location (i.e., position and orientation) of an elongate medical device within the body of a patient, mapping the anatomy of the patient, etc. The system 70 may include various visualization, mapping and navigation components as known in the art, including, for example, an EnSite™ Velocity™ system commercially available from St. Jude Medical, Inc., or as seen generally, for example, by reference to U.S. Pat. No. 7,263,397, or U.S. patent application publication no. 2007/0060833, both of which are hereby incorporated by reference in their entireties as though fully set forth herein.

The system 70 may include an electronic control unit (ECU) 72, an analog-to-digital converter (A-to-D) 74, a lowpass filter (L.P.) 76, a switch 78, a signal generator 80, and a plurality of body surface patch electrodes 82. The system 70 may be electronically and/or mechanically coupled with an elongate medical device 84. The system 70 may be configured for a number of functions for guiding the elongate medical device 84 to a target site within the body of a patient 86, such as the heart 88, and for assessing contact between the elongate medical device 84 and the tissue of the patient 86. The system 70 may further include a conventional set of ECG leads 90 for the capture and measurement of patient ECG data.

The elongate medical device 84 may be one of the catheters 10, 24 described herein (see FIGS. 1-3), or some other elongate medical device. The elongate medical device 84 may have one or more electrodes 92. The one or more electrodes may include a tip electrode 22 (see FIGS. 1-3), one or more ring electrodes 20 (see FIGS. 1-3), and/or another type of electrode. Two or more electrodes 92 may be used as the electrodes A, B illustrated in FIG. 4 and used in the method of FIG. 5.

Referring again to FIG. 6, the signal generator 80 may output an excitation signal for assessing a contact state of an electrode 92. The excitation signal may have a frequency within a range from about 1 kHz to over 500 kHz, more preferably within a range of about 2 kHz to 200 kHz, and even more preferably about 20 kHz, in an embodiment. The excitation signal may be a constant current signal, preferably in the range of between 20-200 μA, and more preferably about 100 μA, in an embodiment. The signal generator 80 may also generate signals involved in, for example, determining a location of the electrodes 92 within the body of the patient.

The ECU 72 may include a memory 94 and a processor 96. The memory 94 may be configured to store data respective of the elongate medical device 84, of the patient 86, and/or other data. Such data may be known before a medical procedure, or may be determined and stored during a procedure. The memory 94 may also be configured to store instructions that, when executed by the processor 96, cause the ECU 72 to perform one or more methods, steps, functions, or algorithms described herein. For example, but without limitation, the memory 94 may include data and instructions for determining impedances respective of one or more electrodes 92 on the elongate medical device 84, as described in conjunction with FIGS. 3 and 4. Such impedances may be used, for example, to assess contact between one or more electrodes 92 and patient tissue.

In addition to impedance calculations and contact state determinations, the system 70 may be configured to determine the position and orientation (P&O) of the elongate medical device 84 (e.g., of a distal end portion of the elongate medical device 84) within the body of the patient 86. Accordingly, the ECU 72 may be configured to control generation of one or more electrical fields and determine the position of one or more electrodes 92 within those fields. The ECU 72 may thus be configured to control signal generator 80 in accordance with predetermined strategies to selectively energize various pairs (dipoles) of body surface patch electrodes 82 and catheter electrodes 92.

Referring to FIGS. 4 and 6, the ECU 72 may include one or more portions of and/or may be configured to perform the functionality of one or more portions of, the detection amplifier 44, such as the op amps 48 and impedance sensor for determining the detected impedance, in an embodiment. Additionally or alternatively, one or more portions of the detection amplifier 44 may be provided in the system 70 in hardware separate from the ECU 72.

Referring again to FIG. 6, the mapping and navigation functionality of the system 70 will be briefly described. The body surface patch electrodes 82 may be used to generate axes-specific electric fields within the body of the patient 86, and more specifically within the heart 88. Three sets of patch electrodes may be provided: (1) electrodes $82_{X1}$, $82_{X2}$, (X-axis); (2) electrodes $82_{Y1}$, $82_{Y2}$, (Y-axis); and (3) electrodes $82_{Z1}$, $82_{Z2}$, (Z-axis). Additionally, a body surface electrode ("belly patch") $82_B$, may be provided as an electrical reference. The body patch electrodes $82_{X1}$, $82_{X2}$, $82_{Y1}$, $82_{Y2}$, $82_{Z1}$, $82_{Z2}$, $82_B$ may be referred to herein generically as a body patch electrode 82 or as the body patch electrodes 82. Other surface electrode configurations and combinations are suitable for use with the present disclosure, including fewer body patch electrodes 82, more body patch electrodes 82, or different physical arrangements, e.g. a linear arrangement instead of an orthogonal arrangement.

Each patch electrode 82 may be independently coupled to the switch 78, and pairs of patch electrodes 82 may be selected by software running on the ECU 72 to couple the patch electrodes 82 to the signal generator 80. A pair of electrodes, for example the Z-axis electrodes $82_{Z1}$, $82_{Z2}$, may be excited by the signal generator 80 to generate an electrical field in the body of the patient 86 and, more particularly, within the heart 88. In an embodiment, this electrode excitation process occurs rapidly and sequentially as different sets of patch electrodes 82 are selected and one or more of the unexcited surface electrodes 82 are used to measure voltages. During the delivery of the excitation signal (e.g., current pulse), the remaining (unexcited) patch electrodes 82 may be referenced to the belly patch $82_B$ and the voltages impressed on these remaining electrodes 82 may be measured. In this fashion, the patch electrodes 82 may be divided into driven and non-driven electrode sets. The low pass filter 76 may process the voltage measurements. The filtered voltage measurements may be transformed to digital data by the analog to digital converter 74 and transmitted to the ECU 72 for storage (e.g. in the memory 94) under the direction of software. This collection of voltage measurements may be referred to herein as the "patch data." The software may store and have access to each individual voltage measurement made at each surface electrode 82 during each excitation of each pair of surface electrodes 82.

Generally, in an embodiment, three nominally orthogonal electric fields may be generated by the series of driven and sensed electric dipoles in order to determine the location of the elongate medical device 84 (i.e., of one or more electrodes 92). Alternately, these orthogonal fields can be decomposed and any pair of surface electrodes (e.g., non-orthogonal) may be driven as dipoles to provide effective electrode triangulation.

The patch data may be used, along with measurements made at one or more electrodes 92 and measurements made at other electrodes and devices, to determine a relative location of the one or more electrodes 92. In some embodiments, electric potentials across each of the six orthogonal patch electrodes 82 may be acquired for all samples except when a particular surface electrode pair is driven. In an embodiment, sampling electric potentials may occur at all patch electrodes 82, even those being driven.

As a part of determining locations of various electrodes, the ECU 72 may be configured to perform one or more compensation and adjustment functions, such as motion compensation. Motion compensation may include, for example, compensation for respiration-induced patient body movement, as described in U.S. patent application publication no. 2012/0172702, which is hereby incorporated by reference in its entirety.

Data sets from each of the patch electrodes 82 and the electrodes 92 are all used to determine the location of the electrodes 92 within the patient 86. After the voltage measurements are made for a particular set of driven patch electrodes 82, a different pair of patch electrodes 82 may be excited by the signal generator 80 and the voltage measurement process of the remaining patch electrodes 82 and electrodes 92 takes place. The sequence may occur rapidly, e.g., on the order of 100 times per second in an embodiment. The voltage on the electrodes 92 within the patient 86 may bear a linear relationship with the position of the electrodes between the patch electrodes 82 that establish the electrical fields, as more fully described in U.S. Pat. No. 7,263,397 referred to above.

In summary, FIG. 6 shows an exemplary system 70 that employs seven body patch electrodes 82, which may be used for injecting current and sensing resultant voltages. Current may be driven between two patches 82 at any time. Positioning measurements may be performed between a non-driven patch 82 and, for example, belly patch $82_B$ as a ground reference. An electrode bio-impedance may be computed according to the following equation (1):

$$BioZ[n \rightarrow m][k] = \frac{V_k}{I_{n \rightarrow m}} \tag{1}$$

where $V_k$ is the voltage measured on electrode k and $I_{n \to m}$ is a known constant current driven between electrodes n and m. The position of an electrode 92 may be determined by driving current between different sets of patches and measuring one or more impedances. Some impedances that may be measured may be according to currents driven between two electrodes 92 on the elongate medical device 84. In one embodiment, time division multiplexing may be used to drive and measure all quantities of interest. Position determining procedures are described in more detail in, for example, U.S. Pat. No. 7,263,397 and publication no. 2007/0060833 referred to above.

In addition to a simple impedance, the systems and methods described herein may be used to determine a complex impedance respective of one or more electrodes on a catheter. Such complex impedances may be used to assess a contact state between an electrode and tissue. For example, as described in U.S. Pat. No. 8,403,925, which is hereby incorporated by reference in its entirety, a complex impedance may be used to determine an electrical coupling index (ECI), which in turn may be used to assess contact between an electrode and tissue.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Although numerous embodiments of this invention have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for assessing contact between a medical device and tissue, the system comprising:
    an electronic control unit (ECU) configured to be coupled to a medical device, the medical device comprising a first electrode and a second electrode, the ECU further configured to select the first electrode as an electrical source and the second electrode as an electrical sink, to cause an electrical signal to be driven between the source and sink, to detect respective electric potentials on the first electrode and the second electrode while the electrical signal is driven, to determine an impedance respective of one of the first electrode and the second electrode according to both of the respective electric potentials, determine a non-binary contact state between the medical device and the tissue based on the determined impedance, and output a signal indicative of the non-binary contact state;
    a display, communicatively coupled to the ECU, and configured to receive the output signal indicative of the non-binary contact state between the medical device and the tissue, and to visualize the non-binary contact state;
    wherein the non-binary contact state is indicative of a degree of contact between the medical device and the tissue; and
    wherein the respective electric potentials are referenced to an electric potential on a third electrode.

2. The system of claim 1, wherein said ECU is configured to determine a first impedance respective of the first electrode according to the respective electric potentials of both the first electrode and the second electrode and to determine a second impedance respective of the second electrode according to the respective electric potentials of both the first electrode and the second electrode.

3. The system of claim 1, wherein said ECU is configured to determine the impedance respective of one of the first electrode and the second electrode further by subtracting the effect of an impedance respective of the other of the first electrode and the second electrode from the electric potential of the one of the first electrode and the second electrode.

4. The system of claim 1, wherein the third electrode is a patch electrode coupled to the body of a patient.

5. The system of claim 1, wherein the third electrode is disposed within the body of a patient.

6. The system of claim 1, further comprising a first operational amplifier and a second operational amplifier, wherein the respective potential on the first electrode is input to said first operational amplifier and the respective potential on the second electrode is input to said second operational amplifier.

7. The system of claim 1, wherein said ECU is further configured to determine the impedance respective of one of the first electrode and the second electrode according to a distance between the first electrode and the second electrode, wherein the distance is known by the ECU.

8. The system of claim 1, further including the first electrode and the second electrode communicatively coupled to the ECU, and configured and arranged to
 contact tissue,
 operate in a bipole arrangement, where one of the electrodes is a sink and the other the source, the bipole arrangement inducing an electrical signal between the first and second electrodes, and
 detect electrical potentials indicative of the impedance between the electrodes and the tissue.

9. The system of claim 1, wherein the display is further configured and arranged to facilitate clinician diagnosis based on the visualized non-binary contact state observed.

10. The system of claim 1, wherein the ECU is further configured to determine an electrical coupling index based on the determined impedance, and the degree of contact between the medical device and the tissue is based on the determined electrical coupling index.

11. A system, comprising:
 an elongate medical device comprising a shaft and a first electrode and a second electrode disposed on or in the shaft; and
 an electronic control unit (ECU) coupled to said elongate medical device and configured to select the first electrode as an electrical source and the second electrode as an electrical sink, to cause an electrical signal to be driven between the source and sink, to detect respective electric potentials on said first electrode and said second electrode while the electrical signal is driven, to determine an impedance respective of one of said first electrode and said second electrode according to the respective electric potentials, to determine the non-binary contact state between the medical device and the tissue based on the determined impedance, and output a signal indicative of the non-binary contact state;
 a display, communicatively coupled to the ECU, and configured to receive the output signal indicative of the non-binary contact state between the medical device and the tissue, and to visualize the non-binary contact state; and
 a patch electrode configured to be disposed on the body of a patient, wherein the respective electric potentials are referenced to an electric potential on said patch electrode; and
 wherein the non-binary contact state is indicative of a degree of contact between the medical device and the tissue.

12. The system of claim 11, wherein at least one of said first electrode and said second electrode is a ring electrode.

13. The system of claim 11, wherein said first electrode is disposed about six millimeters away from the second electrode along the length of said shaft.

14. The system of claim 11, wherein both said first electrode and said second electrode have a radius of about one millimeter.

15. The system of claim 11, wherein said ECU is configured to determine the impedance further according to a known distance between said first electrode and said second electrode.

16. The system of claim 11, wherein said ECU is configured to determine the impedance further according to a known radius of said first electrode or said second electrode.

* * * * *